United States Patent
Getin et al.

(10) Patent No.: US 7,511,263 B2
(45) Date of Patent: Mar. 31, 2009

(54) OBJECT SEPARATION DEVICE USING OPTICAL METHOD

(75) Inventors: Stephane Getin, Grenoble (FR); Alexandra Fuchs, Beaulieu (FR); Guillaume Colas, Grenoble (FR); Stephanie Gaugiran, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 480 days.

(21) Appl. No.: 10/581,484

(22) PCT Filed: Dec. 3, 2004

(86) PCT No.: PCT/EP2004/053261

§ 371 (c)(1),
(2), (4) Date: Jun. 2, 2006

(87) PCT Pub. No.: WO2005/054818

PCT Pub. Date: Jun. 16, 2005

(65) Prior Publication Data

US 2008/0190756 A1  Aug. 14, 2008

(30) Foreign Application Priority Data

Dec. 4, 2003 (FR) .................................. 03 50967

(51) Int. Cl.
*H05H 3/02* (2006.01)
*C07C 7/00* (2006.01)
(52) U.S. Cl. .................. 250/251; 204/157.15
(58) Field of Classification Search .............. 250/251; 204/157.15; 264/112, 259, 299; 422/52; 305/37; 359/15, 566, 296, 434; 385/130; 435/6; 522/146; 430/270.1
See application file for complete search history.

(56) References Cited

U.S. PATENT DOCUMENTS

| | | | |
|---|---|---|---|
| 5,858,192 A | 1/1999 | Becker et al. | |
| 5,888,370 A | 3/1999 | Becker et al. | |
| 5,993,630 A | 11/1999 | Becker et al. | |
| 5,993,632 A | 11/1999 | Becker et al. | |

FOREIGN PATENT DOCUMENTS

| | | |
|---|---|---|
| DE | 19860118 | 9/2000 |
| EP | 0 969 297 | 1/2000 |
| EP | 1 324 645 | 7/2003 |

(Continued)

OTHER PUBLICATIONS

Tanaka, Takuo et al., "Optically Induced Propulsion of Small Particles in a Evenescent Field of Higher Propagation Mode in a Multimode, Channeled Waveguide", Applied Physics Letters, vol. 77, No. 20, pp. 3131-3133, 2000.

(Continued)

*Primary Examiner*—Walter D Griffin
*Assistant Examiner*—Cameron J Allen
(74) *Attorney, Agent, or Firm*—Oblon, Spivak, McClelland, Maier & Neustadt, P.C.

(57) ABSTRACT

A method for separation of particles with different sizes. The method introduces radiation in a waveguide, coupled to a second guide in a coupling area, the radiation entraining all particles towards the coupling area, and separates the particles as they pass into the coupling area.

15 Claims, 7 Drawing Sheets

FOREIGN PATENT DOCUMENTS

| | | |
|---|---|---|
| WO | 0000292 | 1/2000 |
| WO | 00 37920 | 6/2000 |
| WO | 00 69565 | 11/2000 |

OTHER PUBLICATIONS

Kawata, S. et al., "Optically Driven Mie Particles in a Evanescent Field Along a Channeled Waveguide", Optics Letters, vol. 21, No. 21, pp. 1768-1770, 1996.

Ng, L.N. et al., "Propulsion of Gold Nanoparticles on Optical Waveguides", Optics Communications, vol. 208, No. 1-3, pp. 117-124, 2002.

Kawata, Satoshi et al., "Movement of Micrometer-Sized Particles in the Evanescent Field of a Laser Beam", Optics Letters, vol. 17, No. 11, pp. 772-774, 1992.

Ashkin, A, et al., "Observation of Radiation-Pressure Trapping of Particles by Alternating Light Beams" Physical Review Letters, vol. 54, No. 12, pp. 1245-1248, 1985.

Ng, L.N. et al., "Manipulation of Colloidal Gold Nanoparticles in the Evanescent Field of a Channel Waveguide", Applied Physics Letters, vol. 76, No. 15, pp. 1993-1995, 2000.

U.S. Appl. No. 10/581,199, filed Jun. 1, 2006, Getin et al.

U.S. Appl. No. 10/581,483, filed Jun. 2, 2006, Getin et al.

U.S. Appl. No. 10/581,484, filed Jun. 2, 2006, Getin et al.

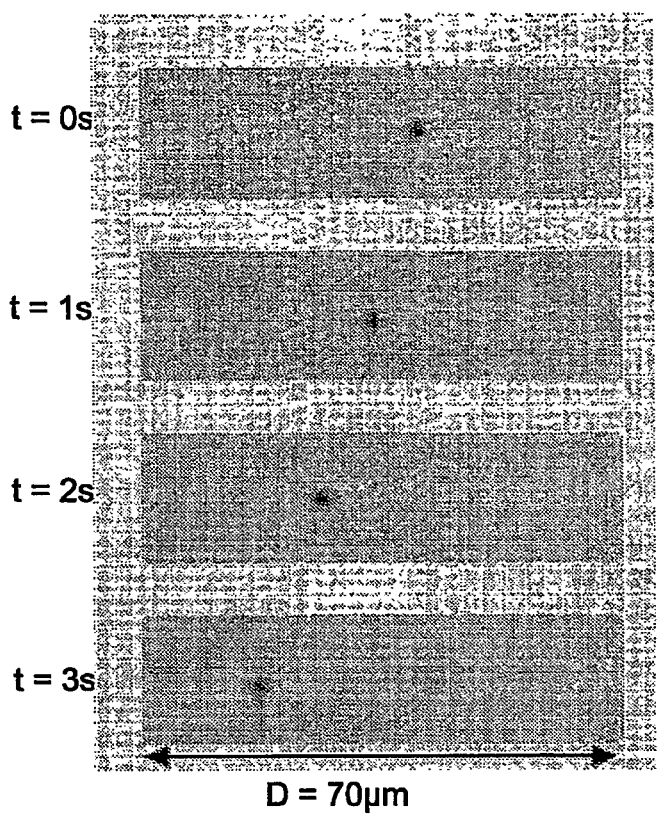
FIG. 9A
FIG. 9B
FIG. 9C
FIG. 9D
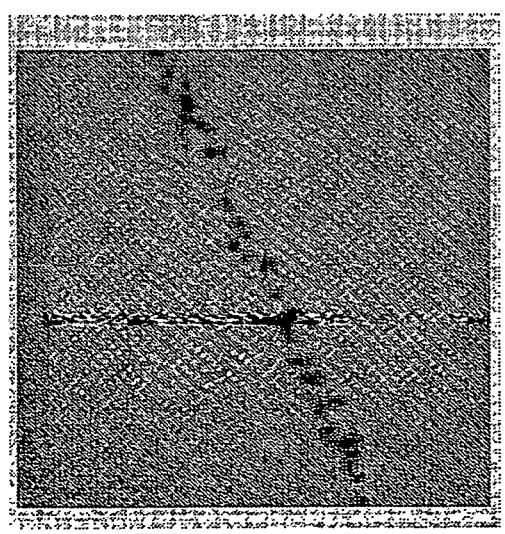
FIG. 10

OBJECT SEPARATION DEVICE USING OPTICAL METHOD

TECHNICAL DOMAIN AND PRIOR ART

This invention relates to the domain of sorting and analysis of small particles. These particles may be cells (biological particles, liposomes, animal or vegetable cells, viruses or micro-organisms), macromolecules (DNA or RNA or proteins) or microballs. Application domains may then be chemical or biomedical analysis or quality control (calibration of micro-particles).

Known approaches in terms of particle cell sorting, such as flow cytometry, have limits particularly for the analysis of rare or very minority cell populations.

The technique of optical clamps for example, described in the article by "Ashkin and Dziedic" entitled "Observation of radiation-pressure trapping of particles by alternating light beams" published in Physics Review Letters, 54(12), 1985, is based on the confinement of a particle (microball, or cell or macromolecule) by the intensity gradient generated at the waist of a continuous laser beam. This operation is made possible by balancing of radiation pressures. Once this operation has been done, the particle is displaced by displacing the beam.

Thus, displacement distances on this type of device are usually limited to a few hundred microns.

Finally, it is impossible to sort metallic particles.

FIG. 1 shows the principle of such a device.

A particle 2 is confined by a beam 4 in a liquid medium 6.

FIG. 2 is a diagram showing a force field generated by the device, on each side of the laser beam 4; the particle is confined in a mechanical force field (induced by the radiation pressure provoked by the electromagnetic field of the laser) which makes it possible to trap it.

This type of device has two disadvantages: displacement of particles is based on use of a dedicated mechanical system, which may be difficult and expensive to set up.

Moreover, it is impossible to make any type of separation of species as a function of their shape or size characteristics, if an automatic or manual recognition device is not used.

Recent work, for example such as that described in the article by T. Tanaka et al., published in Applied Physics Letters, Vol. 77, p. 3131, 2000, makes use of guided optical devices, and suggests the possibility of designing a device for displacement of cells by optical forces.

As illustrated in FIG. 3, this device uses a waveguide 10 with a strip made on a substrate 12. A particle is displaced by a force with photonic pressure, which is proportional to the light intensity at the particle. The particle is held in place in the guide by a force that is proportional to the gradient of the intensity.

If the waveguide is single mode, there is a maximum light intensity at the location at which the particle will be trapped.

The problem arises of finding a new method and a new device for sorting particles easily and efficiently.

In particular, in biology, particles such as balls are frequently fixed to cells. However, marking efficiencies are not perfect and there are always balls in solution that are not fixed and that can be a nuisance. Solutions such as optical clamps cannot be used to perform this separation easily. With these solutions, particles have to be separated one by one. Therefore, another problem that arises is to easily and efficiently separate unfixed particles and cells marked with such particles.

PRESENTATION OF TEE INVENTION

The invention relates to systems for sorting or separating particles or objects, for example with biological interest.

More specifically, the invention relates to a method for the separation of particles with different sizes, immersed in a liquid, this method including:

introduction of radiation in a waveguide, coupled to a second guide in a coupling area, this radiation entraining all particles towards the coupling area, separation of the particles as they pass into the coupling area.

The invention uses at least two waveguides coupled in a coupling area, for example with a length of between 10 μm and 50 μm. The distance between the guides in the coupling area is less than a few micrometres, for example less than 5 μm.

Different sized particles can then be sorted or separated; particles to be sorted or separated are initially located close to an uncoupled portion of the first guide, into which light is injected. This light produces an evanescent wave by which all particles can be displaced. As the distance to the coupling area reduces, an area is created in which there is interaction and disturbance of the profile of the light intensity of the evanescent wave. A "super mode" induced by coupling entrains larger particles towards the second guide.

The light injected into one of the two guides is between the ultraviolet and the infrared.

Particles consisting of microballs and biological cells marked with microballs can be sorted or separated. With the invention, this sorting or separation can be made easily and collectively.

The invention also relates to a particle separation or sorting device comprising two optical guides coupled through a coupling area with a length of between 10 and 50 μm, in which the distance between the guides is less than 5 μm.

The method and device according to the invention use optical forces for sorting particles or for the separation of particles.

Means can also be used to send radiation with a wavelength of between 300 nm and 1.2 μm or even 1 μm and 1.2 μm in one of these guides.

Display means are used to display sorting or separation of particles.

BRIEF DESCRIPTION OF THE FIGURES

FIGS. 9A to 9D, 10, 11A to 11C show experimental results.

DETAILED PRESENTATION OF PARTICULAR EMBODIMENTS

Figure 4:
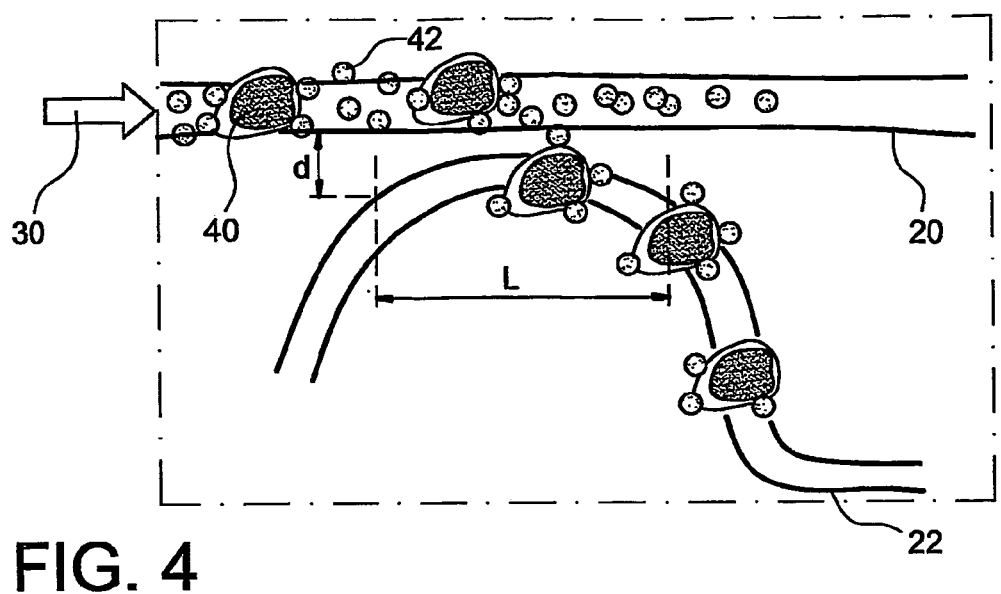
FIG. 4 shows a device according to the invention.

FIG. 4 shows a device according to the invention comprising a first waveguide 20 and a second waveguide 22. Each of these guides may be single mode or multi-mode. The two guides may have different dimensions and may be made of different materials, and in particular have different optical indexes.

Light radiation 39 injected into the guide 20 in a non-coupling area of the guides produces an evanescent wave outside the guide which will mean that particles 40, 42 with different sizes can be displaced, for example some with a size or a diameter between 600 nm or 1 μm and 1.5 μm or 100 μm, others with a size or diameter of the order of 250 nm or between 100 nm and 500 nm. These cells are brought to the neighbourhood of the guide, for example by means of a pipette or a capillary. The assembly is immersed in a liquid medium 41, for example water.

The wavelength of the injected radiation is between the near ultraviolet and the infrared, for example between 300 nm and 1200 nm. For biological particles or cells, wavelengths in the infrared will be used in preference, for example the wavelength of 1064 nm of a YAG laser. The injected power could be of the order of a few tens of milliwatts to a few hundred milliwatts, for example between 50 mW and 1 W, for example close to 150 mW.

The optical index of the largest particles 40 may have be similar to the optical index of the particles 42, at the wavelength used. In this case, the two types of particles will be submitted to an evanescent radiation diffusion effect, that is greater when the particle sixe is larger.

However, if the largest particles 40 have an index similar to the index of the ambient medium, and the index of the small particles 42 is more different from the index of the ambient medium than the cells 40, for the wavelength used, then the smallest particles will usually be displaced faster.

In the infrared range, living cells or biological particles have an index (about 1.37 for cytoplasm, 1.39 for a nucleus, 1.42 for mitochondria as indicated in the article by A. Dunn et al., IEEE Journal of selected topics in quantum electronics vol. 2, No. 4, 1996, p 898-905) similar of the value for water (about 1.33), while smaller gold particles have a much smaller index (about 0.3 at the wavelength of 1064 nm) and have higher absorption (the imaginary part of the index being approximately equal to 7 at the above mentioned wavelength). Therefore advantageously, the cells 40 are marked with particles 42 as illustrated in FIG. 4, to increase the difference between the optical index of the assembly composed of each cell and its marking particles, and the optical index of its environment. For example, the environment may be a liquid such as water (index about 1.33). For biological applications, this liquid may also be a buffer solution or a cell suspension medium, for which the index is also close to 1.33.

For biological cells, polymer particles can be used instead of small gold particles, or any other material can be used on which biological objects can be grafted; once again, these particles are smaller than the cells, and their index is more different from the index of a medium such as water, and can be used as markers.

Since marking efficiencies are not equal to 1, some balls 42 are not fixed on cells. These free balls may be a nuisance in any subsequent operation.

A coupling area with length L, is used to couple part of the radiation 30 injected into the guide 20, in the guide 22. The size L of the interaction area is preferably such that the largest proportion of light goes into the guide 22 due to coupling. In practice, L is of the order of a few tens of micrometres, for example L is between 10 μm and 50 μm.

Coupling is achieved by the distance d between the two guides being less than a few micrometres in the coupling area. This distance actually depends on the wavelength. But for wavelengths of about 1 μm, the value d can be assumed to be <1 μm, or for example between 500 nm and 5 μm.

The coupling area produces a disturbance of the light intensity profile at the guide surface.

Figure 5A:
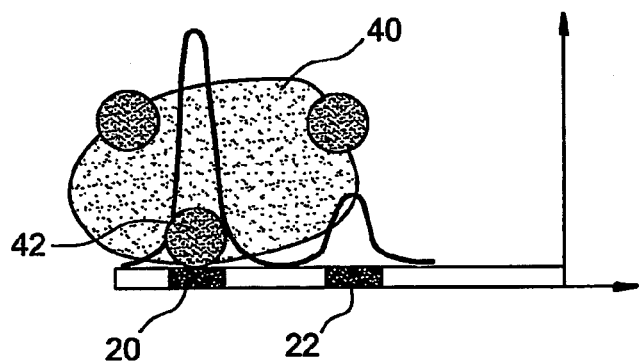
FIGS. 5A and 5B represent the coupling effect on particles.
Figure 5B:
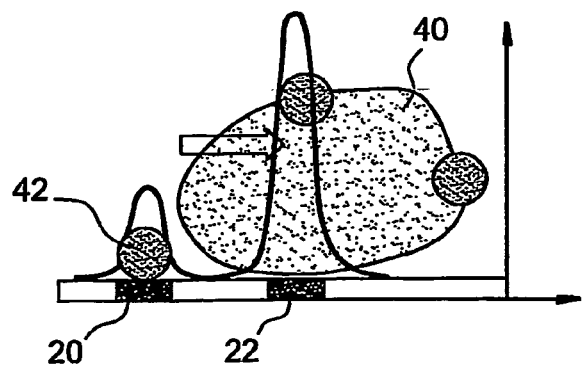

FIG. 5A shows the situation before coupling; this figure shows the profile of the evanescent wave, located mainly above the guide 20, and a cell 40 and a ball 42.

Coupling causes redistribution of the light intensity between the two guides, towards the guide 22. The cell 40 is then entrained towards this guide 22 as shown by the arrow 44. If the difference between its index and the index of the ambient medium is small, it will be entrained better if it is marked with balls 42 for which the difference, at the wavelength used, between the optical indexes of the balls and the ambient medium is greater than the difference between the optical indexes of the cells 40 and the ambient medium.

Particles or objects are then separated as a function of their size. The smallest particles remain on the guide 20 even if their velocity is lower, and gradient forces keep them confined above the guide 20.

However, for the largest particles such as cells 40 and the balls that mark them, the "super mode" is induced by coupling, and the particles will search for a new equilibrium position, which will bring them preferentially towards the guide 22.

Thus, a particle sort or separation is made as a function of the particle size. The particles are then entrained outside the coupling area by the radiation from each guide.

Similarly, a sort would be made between large particles and small particles, if these two particle types have a comparable optical index for the wavelength injected into the guide.

Figure 6A:
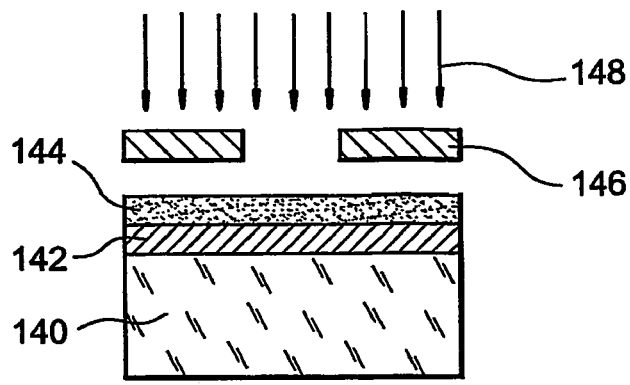
FIGS. 6A to 6D, 7 represent steps in the production of a device according to the invention.
Figure 6B:
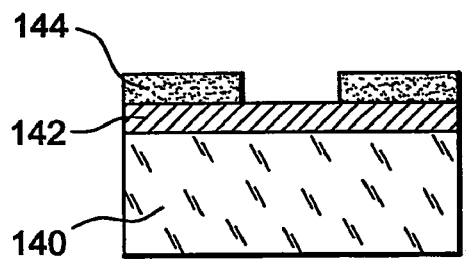
Figure 6C:
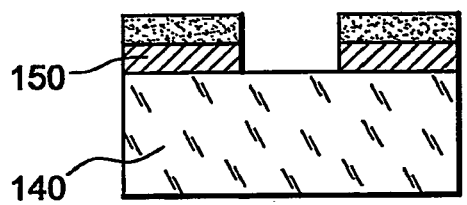
Figure 6D:
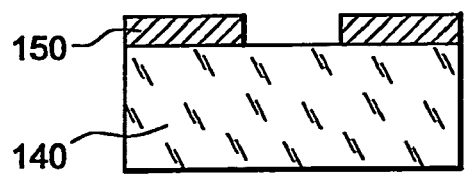
Figure 7:
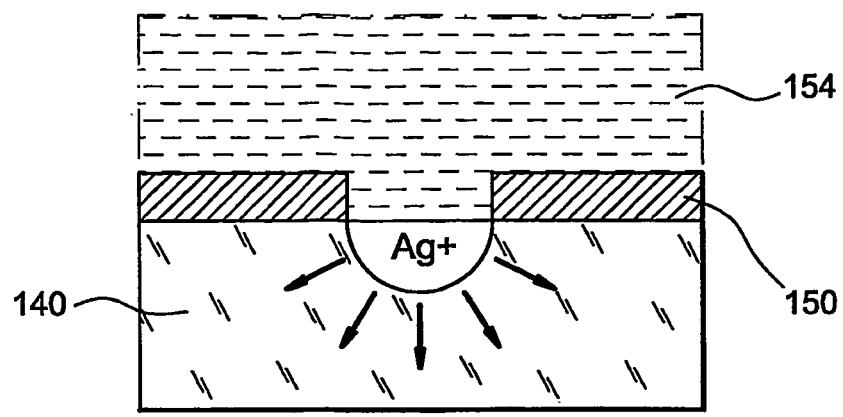

A method for making a guide will now be described with reference to FIGS. 6A to 7.

Firstly (FIG. 6A), a layer of aluminium 142 (obtained for example by evaporation or sputtering), is deposited on a glass surface 140 followed by a layer 144 of photoresist resin (deposition by Spin Coating). A chromium lithography mask 146 is then brought into contact with the resin layer under a vacuum. The mask represents the negative of the final pattern (the guide structure).

The mask is then illuminated using incoherent radiation 148 for which the central wavelength is for example located at about 350 nm and for which the resin is a photoresist resin. The chemical structure of the part that is not concealed by the mask is modified.

The plate is then dipped into a solution that will develop the resin 144. Thus, the areas on which the chemical structure was modified by insolation are etched (FIG. 6B).

The plate is then dipped in an aluminium etching solution (AluEtch). This solution does not etch the resin. Thus, only the previously developed parts are etched (FIG. 6C).

Finally, the resin is dissolved in acetone. Only the pattern 150 remains on the plate (FIG. 6D).

An ion exchange step is then carried out to form the waveguide.

The plate is then immersed in a salt bath containing silver nitrate and sodium nitrate. The proportion between these salts determines the silver content that is exchanged in the glass 140. The bath generally contains between 10% and 50% of silver depending on the application. Since the salt melting temperature is about 310° C., the exchange step is carried out at between 320° C. and 350° C. (FIG. 7).

The aluminium mask pattern 150 is then removed for example by etching. Annealing can possibly be done; the glass plate is heated without any contact with a bath. This step enables silver ions to penetrate more deeply towards the inside of the glass plate.

Figure 1:
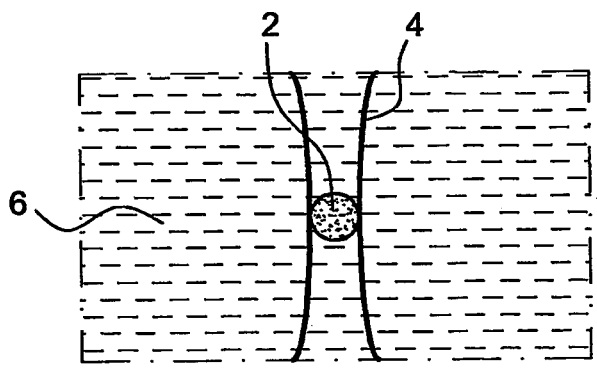
FIGS. 1 to 3 illustrate known techniques according to prior art.
Figure 2:
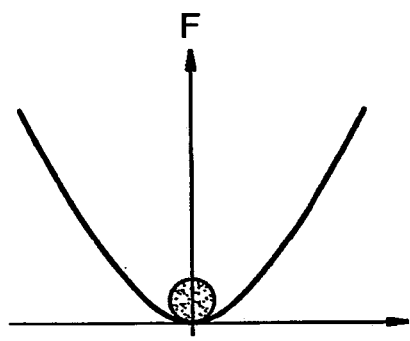
Figure 3:
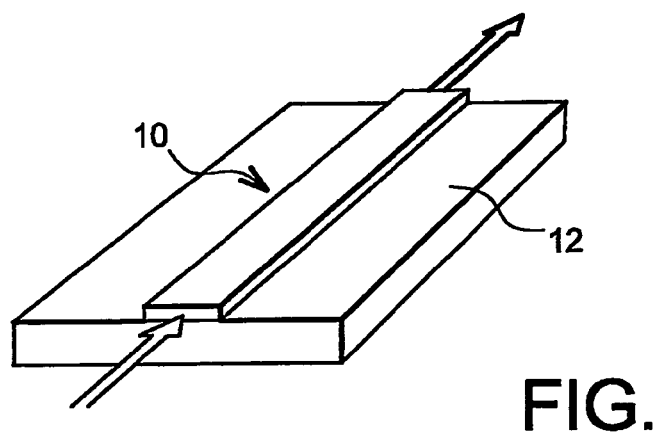

Two guides 20, 22 like those shown in FIG. 1 can be made in this way.

Other methods could also be used, for example to make guides on a silicon substrate.

Braking forces on particles caused by friction with the upper surface of the guide can be reduced, by coating the guide with a special coating, for example a thin Teflon based layer.

One example application can be described in biology.

In a heterogeneous cell sample, an attempt is made to isolate a given sub-population characterised by a specific phenotype, for example the presence of a certain type of surface macromolecules, for example such as proteins. Furthermore, probe molecules such as antibodies are available capable of recognising and bonding with these phenotypic markers with a very strong affinity. In the case of antibody type probe molecules, the phenotypic markers are called antigens. Antibodies are fixed by means known to those skilled in the art to balls chosen for their particular characteristics, for example gold balls. These functionalised gold balls are then grafted onto the surface of cells, for example these cells may be lymphocytes isolated from blood and that are to be sorted.

The marked cells are deposited in a chamber, on the chip (for example by a focusing device integrated into the cover). The chamber may for example be a device of the Gene Frame® type (Abgene®). This small self-sticking chamber is very simple and has a joint system impermeable to gas, providing resistance at temperatures up to 97° C., and prevents the loss of reagent due to evaporation. It is usually used for hybridising and in situ amplification procedures in biology.

Laser light is injected into the guide 20. The chosen wavelength is within the far red/near infrared range, a transparent biological spectral region that ensures viability of cells after treatment; (no absorption by biological molecules or water).

Cells and unfixed balls are sorted as described above.

Marked cells are displaced to an analysis/recuperation window. Biological particles may be recovered, for example by fluid means (recuperation by capillary) or more conventional means (recuperation by pipette at a recuperation chamber adapted to the size of the cone).

In general, observation means may be provided, for example a CCD camera located above the guides. These means enable monitoring of the sort made as described above.

Figure 8:
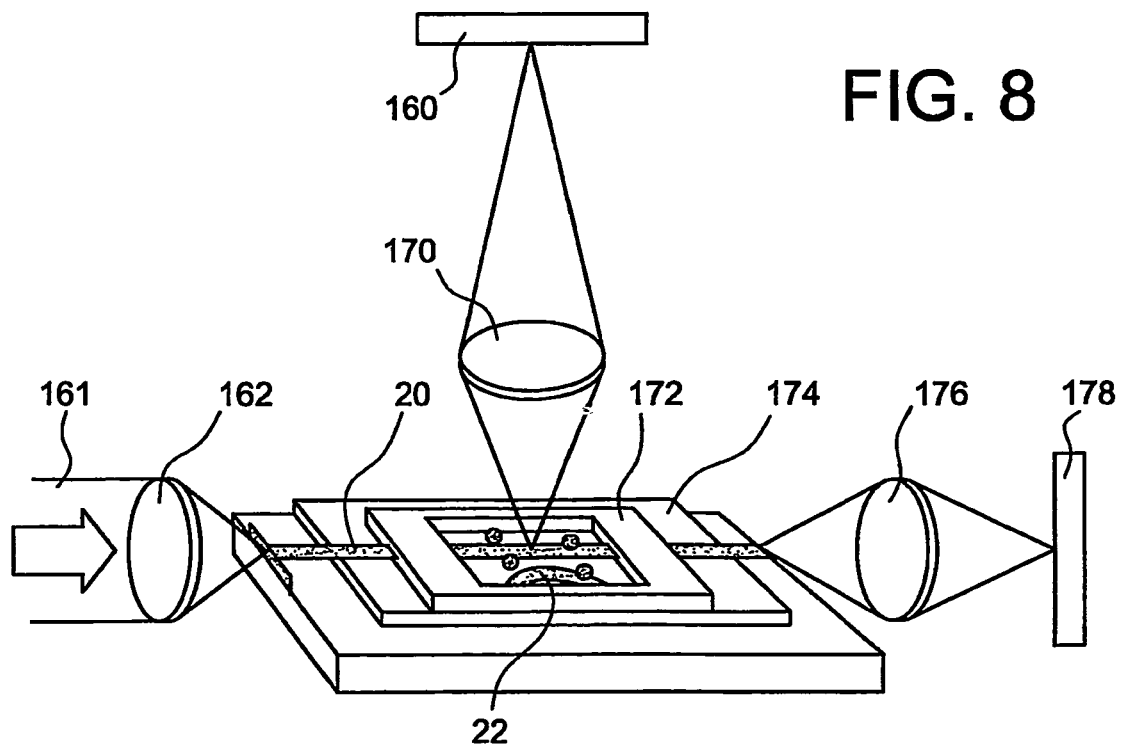
FIG. 8 shows the use of a device according to the invention.

FIG. 8 shows a sort system incorporating a guide system according to the invention. An objective 162 focuses a laser beam 161 (for example a YAG beam at 1064 nm) in a guide 20. The particles to be sorted are contained in a chamber 172 located on a slide 174. A second waveguide 22 is arranged as described above so as to create a coupling area between the two guides. A camera 160 is used to make an image of the separation area, for example using a focusing device or a zoom 170. Means 176, 178 (objective, camera) of forming an image of the transmitted radiation may also be placed at the output from the device.

The invention is applicable not only to sorting of marked cells, but also to other domains, for example calibration of balls or microballs, particularly made of latex or gold.

Another example embodiment will be given. In this example, the waveguides used are surface guides made by a potassium ion exchange (glass slide substrate). These ions are produced at a temperature of 280° C. for an exchange time of 2 h 15. Losses of these guides are of the order of 0.2 to 0.5 dB/cm at a wavelength of 1064 nm.

The displaced particles to be concentrated are glass balls with a refraction index of 1.55 and a diameter of 2 μm, or gold balls with a diameter of 1 μm.

The device used is of the type shown in FIG. 8. Light is coupled through the edge using a continuous YAG laser at 1064 nm (P=10 W) and balls are observed through the top using a zoom system 170 coupled to a video camera 160 for monitoring their displacement.

Experiments carried out on 1 μm diameter gold balls have demonstrated spontaneous grouping of balls on the guide followed by their displacement at velocities of the order of 4 μm/s along the guide. Similarly, the possibility of grouping and displacing glass balls is demonstrated. Thus, FIGS. 9A to 11C illustrate:

FIGS. 9A to 9D; displacement of metallic particles over a distance of 70 μm, at t=0 s, 1s, 2 s, 3 s.

FIG. 10: a metallic particles concentration effect.

Figures 11A, 11B, 11C:
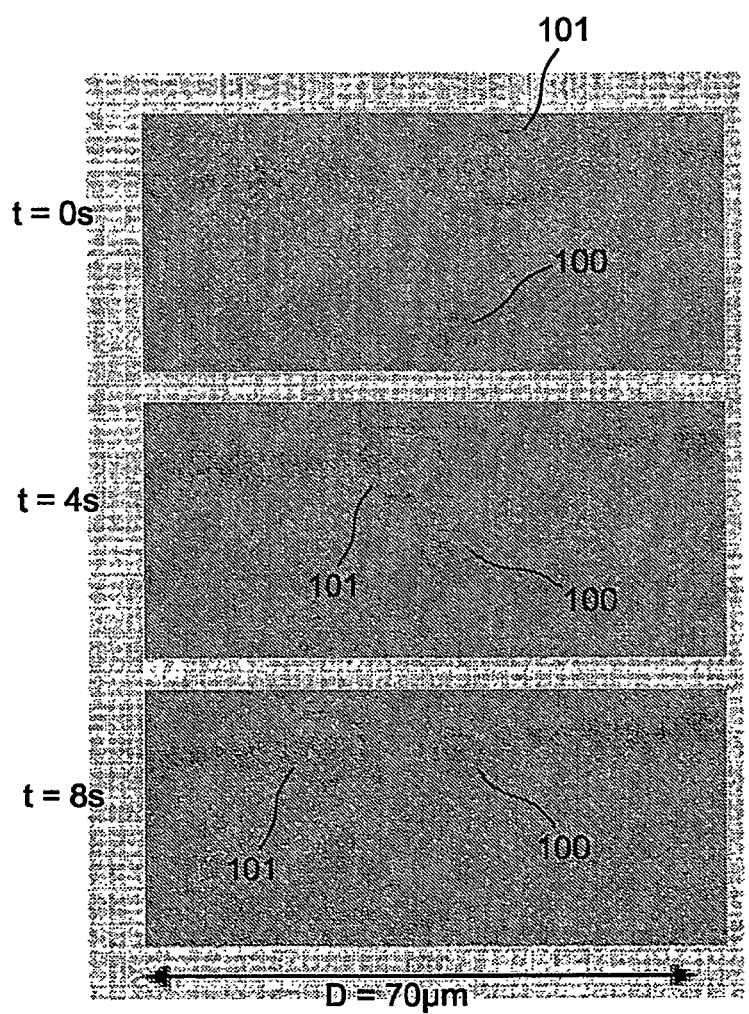

FIGS. 11A to 11C: progressive grouping of glass balls (100, 101) along a 70 μm portion of the guide, at t=0 s, 4 s, 8 s successively.

These results may advantageously be used in the context of a method according to the invention, due to grouping of particles that facilitates separation.

Figure 12A:
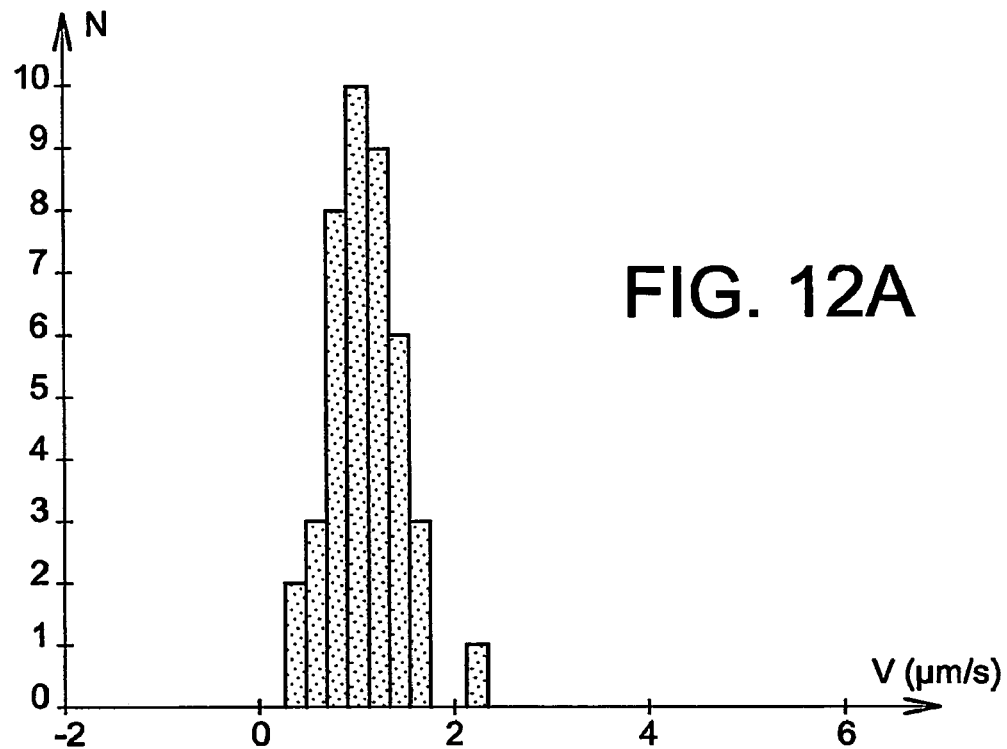
FIGS. 12A and 12B show displacement velocity histograms of gold particles for two different polarisations.
Figure 12B:
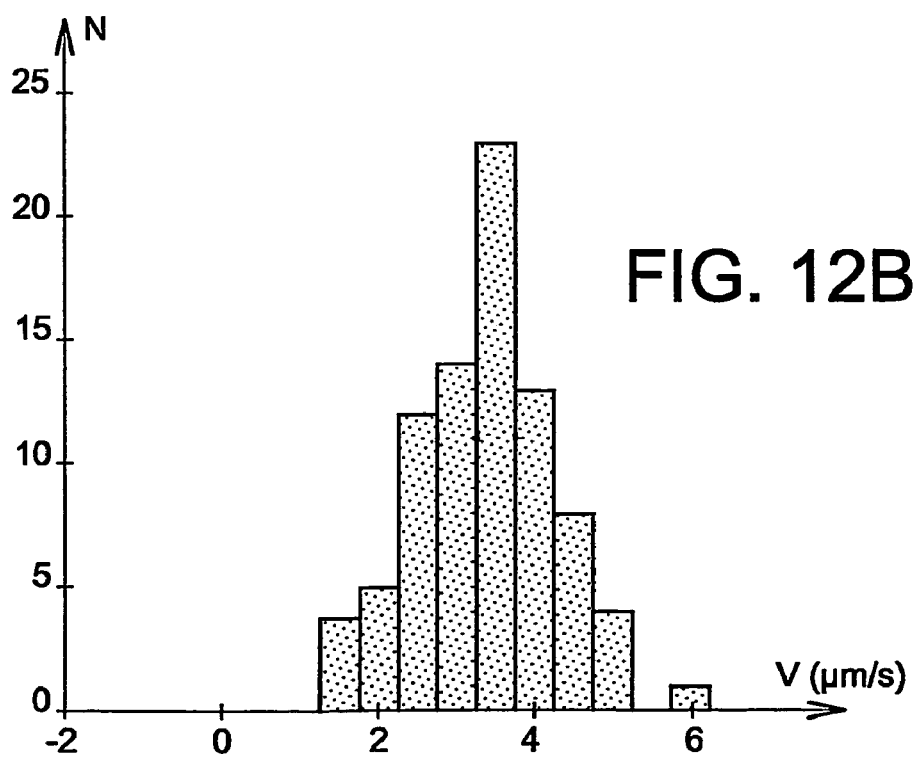

Furthermore, it is observed that the polarisation of light propagated in a guide has an influence on the average velocities of metallic particles (for example gold particles of 1 μm diameter). FIGS. 12A and 12B each show a histogram of gold ball displacement velocities in TE polarisation for FIG. 12A, for which the average velocity is 1.07 μm/s±0.35 and in TM polarisation for FIG. 12B, for which the average velocity is 3.46 μm/s±0.81.

Therefore, the results indicate a displacement velocity approximately 3 times greater for TM (transverse magnetic mode than for TE (transverse electrical) mode. Therefore, for equal injection power, polarisation of light injected into the waveguide can significantly modify the velocity of gold particles.

Once again, these results may advantageously be used in the context of a method according to the invention, due to the improved sort or separation that is possible due to the polarisation effect.

The invention claimed is:

1. A method for separation according to size of particles with different sizes, immersed in a liquid, the method comprising:

introducing a radiation in a waveguide, coupled to a second guide in a coupling area, the radiation entraining all particles towards the coupling area; and separating the particles as they pass into the coupling area.

2. A method according to claim 1, wherein a distance between the two guides in the coupling area is less than 5 μm.

3. A method according to claim 1, wherein a length of the coupling area is between 10 μm and 50 μm.

4. A method according to claim 1, wherein the particles are cells or macromolecules or microballs.

5. A method according to claim 1, wherein the introduced radiation is in a spectral range between near ultraviolet and infrared.

6. A method according to claim 1, wherein the particles are microballs, and microball marked cells, and the radiation is in the infrared range.

7. A method according to claim 1, wherein a diameter of the particles is between 100 nm and 500 nm, or between 600 nm and 1.5 μm, or between 1 μm and 100 μm.

8. A method according to claim 1, wherein the liquid in which the particles are immersed is water or a cell suspension medium.

9. A method according to claim 1, wherein some of the particles are metallic or marked by metallic particles.

10. A method according to claim 9, wherein some of the particles are gold particles or marked by gold particles.

11. A method according to claim 1, wherein the radiation introduced in the waveguide is polarized in transverse magnetic mode.

12. A particle separation device, comprising:

two optical guides coupled by a coupling area with a length between 10 μm and 50 μm, a distance between the guides being between 500 nm and 5 μm.

13. A device according to claim 12, further comprising a radiation source with a wavelength of between 300 nm and 1.2 μm, or 1 μm and 1.2 μm, in one of the two optical guides.

14. A device according to claim 12, further comprising a radiation source polarized in transverse magnetic mode in one of the two optical guides.

15. A device according to claim 12, further comprising means for displaying separation of particles.

* * * * *